United States Patent [19]

Negus et al.

[11] Patent Number: 5,685,857

[45] Date of Patent: Nov. 11, 1997

[54] THORACOSCOPIC CANNULA SYSTEM

[75] Inventors: Charles Christopher Negus, Taunton; Robert L. Rudko, Holliston; Stephen J. Linhares, Taunton, all of Mass.

[73] Assignee: PLC Medical Systems, Inc., Franklin, Mass.

[21] Appl. No.: 621,006

[22] Filed: Mar. 22, 1996

[51] Int. Cl.$^6$ .................................................. A61M 5/178
[52] U.S. Cl. ............................ 604/170; 604/164; 604/174
[58] Field of Search ................................ 604/164, 170, 604/27, 51, 117, 158, 174, 280

[56] References Cited

U.S. PATENT DOCUMENTS 4,871,356  10/1989  Haindl et al. .......................... 604/280
5,391,156   2/1995  Hildwein et al. ...................... 604/164

Primary Examiner—Robert A. Hafer
Assistant Examiner—Luke Yeh
Attorney, Agent, or Firm—Iandiorio & Teska

[57] ABSTRACT

A thoracoscopic cannula system includes a cannula having an enlarged limiter flange and an elongated hollow tube for insertion between the ribs of a thoracic patient; the tube includes first and second opposed concave recesses for snap-fitting and interlocking with the adjacent ribs to securely anchor it; and an introducer including an elongated member slidably received in the hollow tube with a stop flange at one end to limit movement of the introducer through the tube and a beveled, blunted surface at the other end for gently penetrating and leading the cannula through an incision between the ribs of the patient.

4 Claims, 5 Drawing Sheets

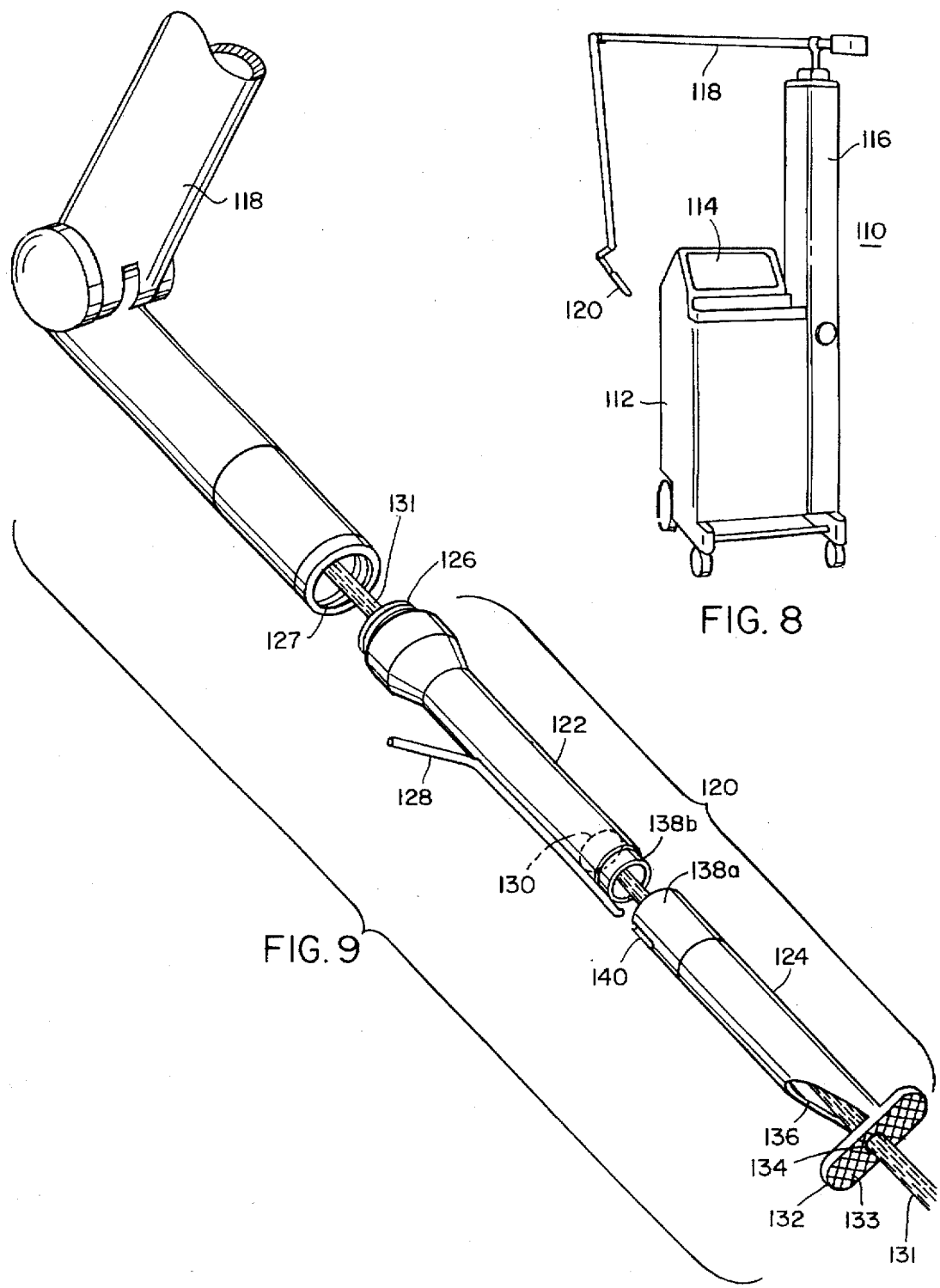

THORACOSCOPIC CANNULA SYSTEM

FIELD OF INVENTION

This invention relates to an improved thoracoscopic cannula system, and more particularly to such an improved thoracoscopic cannula system for use in transmyocardial revascularization (TMR).

BACKGROUND OF INVENTION

Video assisted thoracic (VAT) surgery such as transmyocardial revascularization (TMR) requires that a handpiece be inserted between the ribs of a patient to contact the wall of the beating heart. With the handpiece inserted in the incision, bleeding around the incision causes blood to drip down on the optics and openings of the handpiece and interfere with the TMR. Because of this the handpiece has to frequently be removed, cleaned and reinserted. Further, the handpiece is moved around inside the incision to reposition the contact with the heart wall for each new channel to be created. This constantly insults the incision walls and increases and prolongs the pain and suffering of the patient. Cannulas presently used in thoracic surgery are easily squeezed out by the pressure of the ribs and they cannot accommodate the TMR handpiece.

SUMMARY OF INVENTION

It is therefore an object of this invention to provide an improved thoracic cannula system.

It is a further object of this invention to provide such an improved thoracic cannula system which virtually eliminates the contamination of the handpiece with blood from the incision and the insult to the tissue around the incision.

It is a further object of this invention to provide such an improved thoracic cannula system which snap-fits and securely interlocks with the ribs of the patient.

The invention results from the realization that a thoracic cannula system for VAT TMR which virtually eliminates blood contamination of the handpiece and insulting of the tissue around the incision can be effected by using a cannula which snap-fits between adjacent ribs and accommodates an introducer for aiding in installing the cannula between the ribs.

This invention features a thoracoscopic cannula system including a cannula having an enlarged limiter flange and an elongated hollow tube for insertion between the ribs of a thoracic patient. The tube includes first and second opposed concave recesses for snap-fitting and interlocking with the adjacent ribs to securely anchor it. An introducer includes an elongated member slidably receivable in the hollow tube with a stop flange at one end to limit movement of the introducer through the tube. The elongated member also includes a beveled, blunted surface at the other end for gently penetrating and leading the cannula through an incision between the ribs of the patient.

In a preferred embodiment the stop flange and limiter flange may be coplanar to provide a common surface for applying an insertion force. The introducer may be generally oblong in cross-section. The tube may be beveled proximate the limiter flange for self-guiding the introducer and replacement instruments.

DISCLOSURE OF PREFERRED EMBODIMENT

Other objects, features and advantages will occur to those skilled in the art from the following description of a preferred embodiment and the accompanying drawings, in which:

FIG. 8 is a three-dimensional view of a laser system which utilizes the cannula system of this invention;

FIG. 9 is an enlarged, more detailed, exploded three-dimensional view of a portion of the articulated arm and handpiece in FIG. 8.

Figure 1:
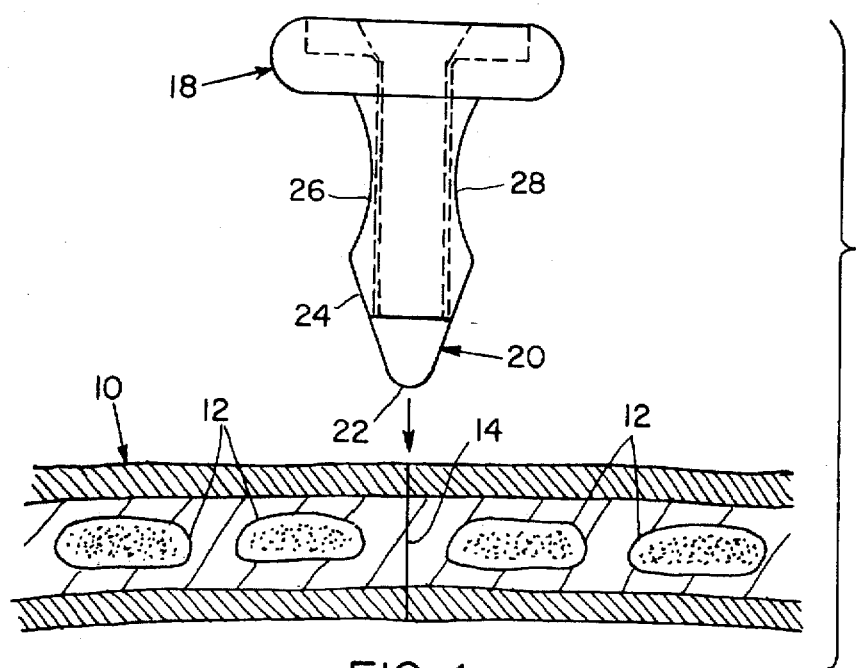
FIG. 1 is a schematic side elevational view of the cannula system according to this invention about to be inserted in an incision between the ribs of a patient.
Figure 2:
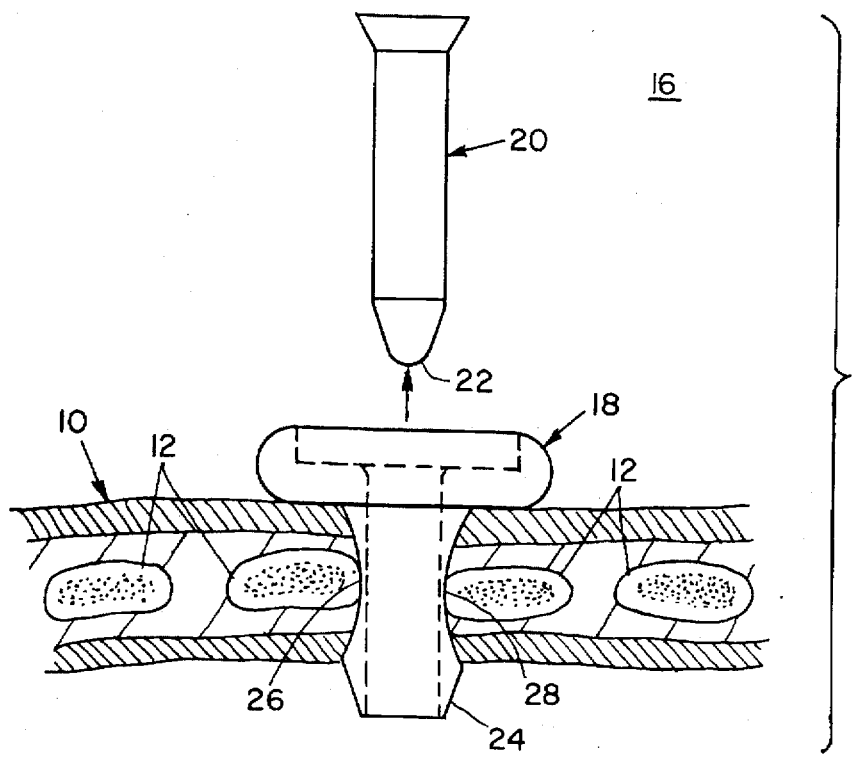
FIG. 2 is a view similar to FIG. 1 with the cannula system inserted between the ribs and the introducer being removed from the cannula.

There is shown in FIG. 1 a cross-section of the rib cage 10 of a patient showing a number of ribs 12 in end section. An incision 14 has been made parallel to the ribs and approximately two inches long. The cannula system 16 according to this invention including cannula 18 and introducer 20 is poised above incision 14 and is about to be inserted therein. Introducer 20 has a gently rounded blunt nose 22 for gently leading the distal end 24 of cannula 18 into and through incision 14. Opposing recesses 26 and 28 in cannula 18 are provided to snap-fit between a pair of adjacent ribs as shown in FIG. 2 after the cannula system has been fully inserted. This snap-fitting action interlocks cannula 18 with the adjacent ribs so that they cannot be easily dislodged or jarred loose. Following this, introducer 20 can be removed and any manner of surgical instruments, viewing agents or other aids for surgeons may be introduced through cannula 18.

Figure 3:
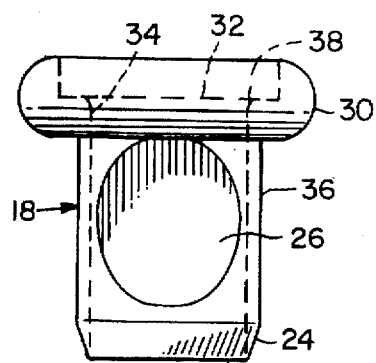
FIG. 3 is a from elevational view of the cannula of FIGS. 1 and 2.
Figure 4:
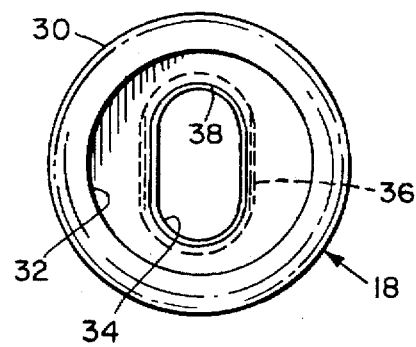
FIG. 4 is a top plan view of the cannula of FIG. 3.
Figures 5A, 5B:
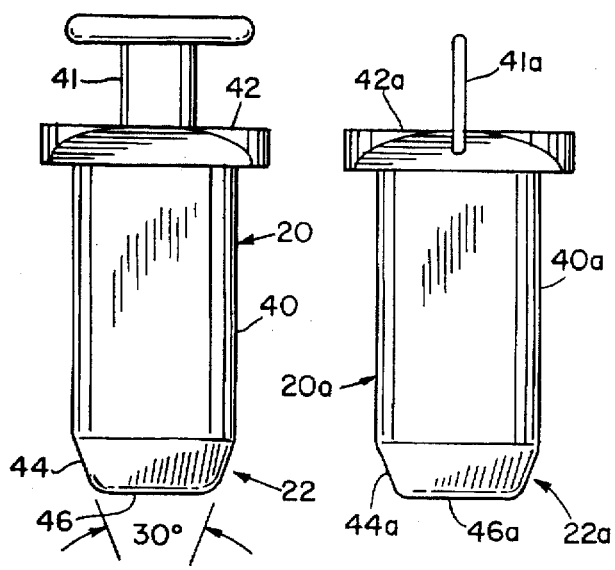
FIG. 5A is a side elevational view of the introducer of FIGS. 1 and 2.
FIG. 5B is a side elevational view of an alternative construction of the introducer.
Figures 6A, 6B:
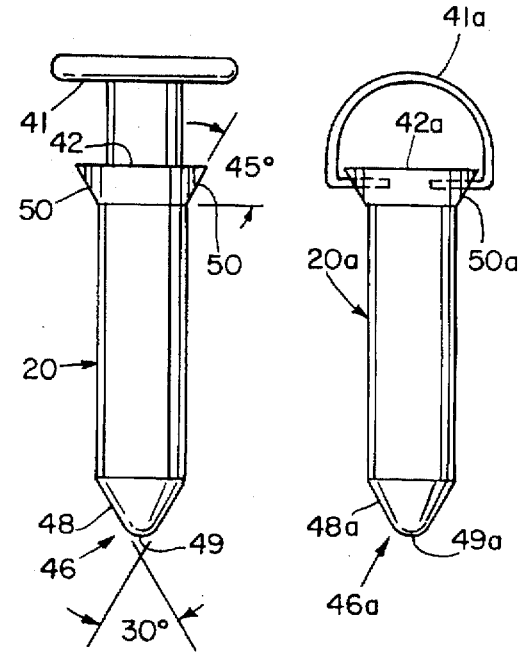
FIG. 6A is an end elevational view of the introducer of FIG. 5A.
FIG. 6B is an end elevational view of the introducer of FIG. 6A.

Cannula 18, FIG. 3, includes a circular stop flange 30 which may rest against the patient's chest wall and prevent complete passage of the cannula into the patient's body cavity. Circular stop flange 30 includes a circular recess 32 which communicates with one end of the hole 34 through hollow tube 36 that extends from stop flange 30. The distal end 24 of elongated tube 36 is tapered to ease its insertion into an incision. The upper inside end of tube 36 at bore 34 is beveled as at 38 to effect a self-guiding or self-centering facility for introducer 20 as well as other surgical instruments and aids. The bore 34 in tube 36 is oblong in shape as can be seen in FIG. 4, which also amply demonstrates the circular nature of stop flange 30 and recess 32. Introducer 20, FIG. 5, also includes an elongate member 40 shaped to slidably fit in bore 34 of cannula 18. A knob 41 is provided for ease of gripping. The upper end of elongated member 40 is connected to limiter flange 42 which limits the movement of introducer 20 through bore 34 of cannula 18. The distal end of elongated member 40 at 22 is gently tapered as at bevel 44 at approximately 30° and has a blunt end 46. In end view, FIG. 6, it can be seen that introducer 20 also contains a bevel 48 of approximately 30° in the end dimension and has a gently rounded radius 49 at blunt end 46. Limiter flange 42 is undercut at chamfers 50 on both sides to aid in gripping when it is to be withdrawn from cannula 18. Introducer 20a, FIGS. 5A and 6A, may have an "O" ring instead of knob 41.

Figure 7:
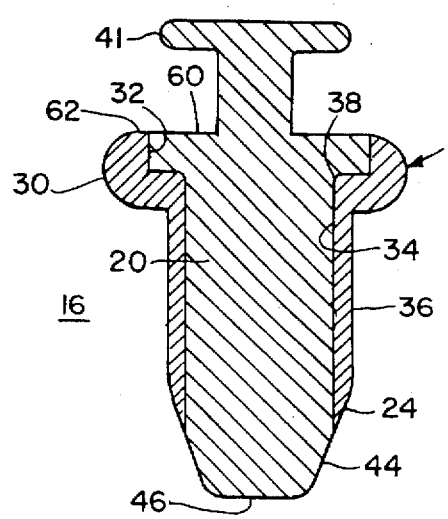
FIG. 7 is a cross-sectional view of the cannula system of this invention with the introducer installed in the cannula.

When fully assembled, as shown in the side cross-sectional view of FIG. 7, introducer 20 fully nests in cannula 18 so that the introducer top surface 60 and the top surface 62 of cannula 18 form a solid surface on which the surgeon can exert force to press cannula system 16 through an incision into the chest of a patient. The oblong shape of the hole or bore 34 in cannula 18 will accommodate the handpiece of a TMR handpiece assembly as shown and described in FIGS. 8–11.

There is shown in FIG. 8 a surgical laser system 110 which includes a power supply and control 112 operated through control and monitor screen 114 to operate laser 116. The output from laser 116 is directed through articulated arm 118 to handpiece assembly 120 typically held by the operator or surgeon to direct the beam at the desired target.

Handpiece assembly 120, FIG. 9, includes barrel 122 and handpiece 124. Barrel 122 includes threaded potion 126 for connection to articulated arm 118 at threaded portion 127, and purge tube 128 for introducing a purge gas into handpiece 124. Handpiece 124 includes contacting wall 132 having a knurled surface 133 for preventing slippage of handpiece 124 on the heart during surgery. There is an aperture 134 in contacting wall 132 through which laser beam 131 exits to strike the heart. Lens 130, shown in phantom in barrel 122, focuses laser beam 131 at a predetermined distance, typically at or near aperture 134. Handpiece 124 also includes cutout portion 136 through which the user can view the beam as it enters aperture 134. Cutout portion 136 also acts as a venting hole for the ablative plume which rises from the heart or other tissue struck by the laser beam 131. Handpiece 124 includes coupling portion 138a which slides over coupling portion 138b of barrel 122 in order to effect a friction fit. There is a slot 140 in coupling portion 138a which accepts the distal end of purge tube 128.

In accordance with this invention, barrel 122 and handpiece 124 typically have diameters in the range of ⅜ inch to ⅝ inch. This allows the handpiece assembly to be slid between adjacent ribs of a patient in order to access the heart without opening the chest cavity. Generally, the space between ribs of a patient is approximately 0.5". As can be seen in the figure, contacting wall 132 of handpiece 124 is formed such that the width of the contacting wall is the same as the diameter of handpiece 124 while the length of contacting wall 132 is approximately twice the diameter of handpiece 124. This increases the area of contact with the heart and therefore decreases the pressure of force per unit area on the heart. It also provides a more stable platform by which to maintain perpendicularity between the beam 131 and the heart wall and reduces the chances of the handpiece puncturing or otherwise damaging the heart tissue. However, the narrow width of contacting wall 132 allows handpiece assembly 120 to be slid either between adjacent ribs of the patient or into the aforementioned cannula.

Purge tube 128 is connected to a purge gas source which provides a gas such as carbon dioxide under a gentle flow, typically one to three liters per minute, to create a back pressure from lens 130 forward into handpiece 124. This keeps any debris from the ablation from contacting and obscuring or damaging lens 130.

Although handpiece assembly 120 has been shown with handpiece 124 as a straight member, this is not a necessary limitation of the invention: handpiece 124 may be constructed at any desired angle. For example, handpiece 124a, FIG. 10, may include a right angle configuration so that contacting wall 132a and aperture 134a are facing at a right angle to the path of laser beam 131. A reflective surface 142 is provided to reflect the beam from an incoming path parallel to axis 144 to the outgoing path parallel to axis 146. One or more vent holes 148 may be provided for exhausting gas and ablated tissue aided by the back pressure caused by the introduction of the purge gas through purge tube 128. In this embodiment, reflective surface 142 is enclosed as much as possible in order to minimize contamination from body fluids prior to firing the laser.

In the preferred embodiment, barrel 122 is formed of stainless steel due to its strength, its ability to be sterilized repeatedly and its ability to withstand heat from the unfocused laser before it is focused by lens 130. Purge tube 128 is also formed of stainless steel and is typically welded to barrel 122. Handpiece 124 is typically injection molded of medical grade clear acrylic. This allows the surgeon to monitor the laser beam as it passes through the handpiece, allows more effective cleaning of the inside of the handpiece during surgery and enhances the disposability of the handpiece. Coupling portion 138a of handpiece 124, however, is formed of the same stainless steel as barrel 122. This allows for a tighter friction fit between handpiece 124 and barrel 122 which is not affected by changes in temperature due to the heat of the laser. Threaded portion 126 of barrel 122 is typically formed of an electrical insulating material such as Delrin to electrically insulate the patient from the laser system, and to avoid additional grounding locations for electrocautery devices used on the patient. Also, lens 130 has a five-inch focal length which focuses beam 131 at aperture 134 in the case of the embodiment of FIG. 9 and at aperture 134a in the case of the embodiment of FIG. 10.

Figure 10:
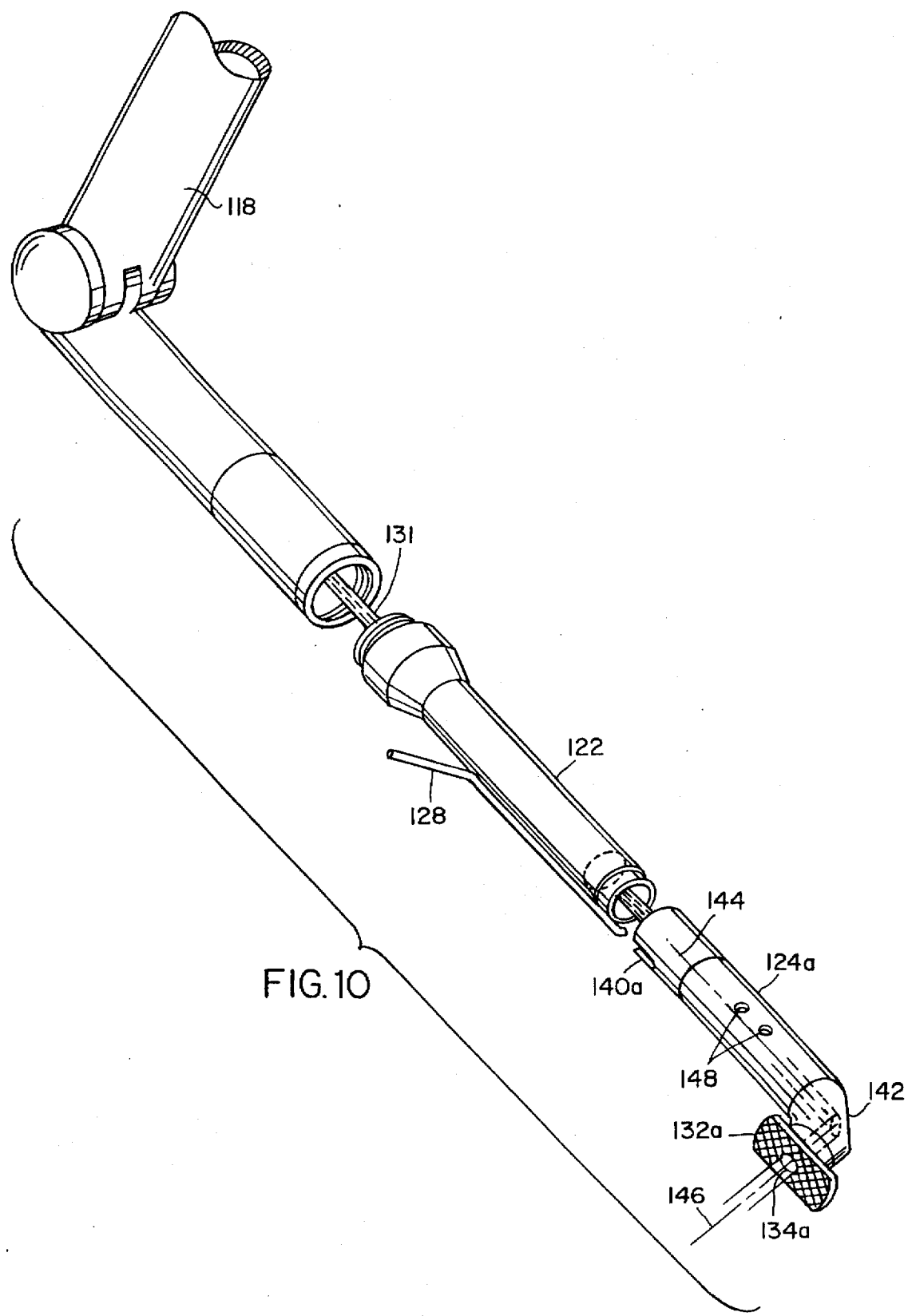
FIG. 10 is an enlarged, more detailed, exploded three-dimensional view of a portion of the articulated arm in FIG. 8 and another form of handpiece.
Figure 11:
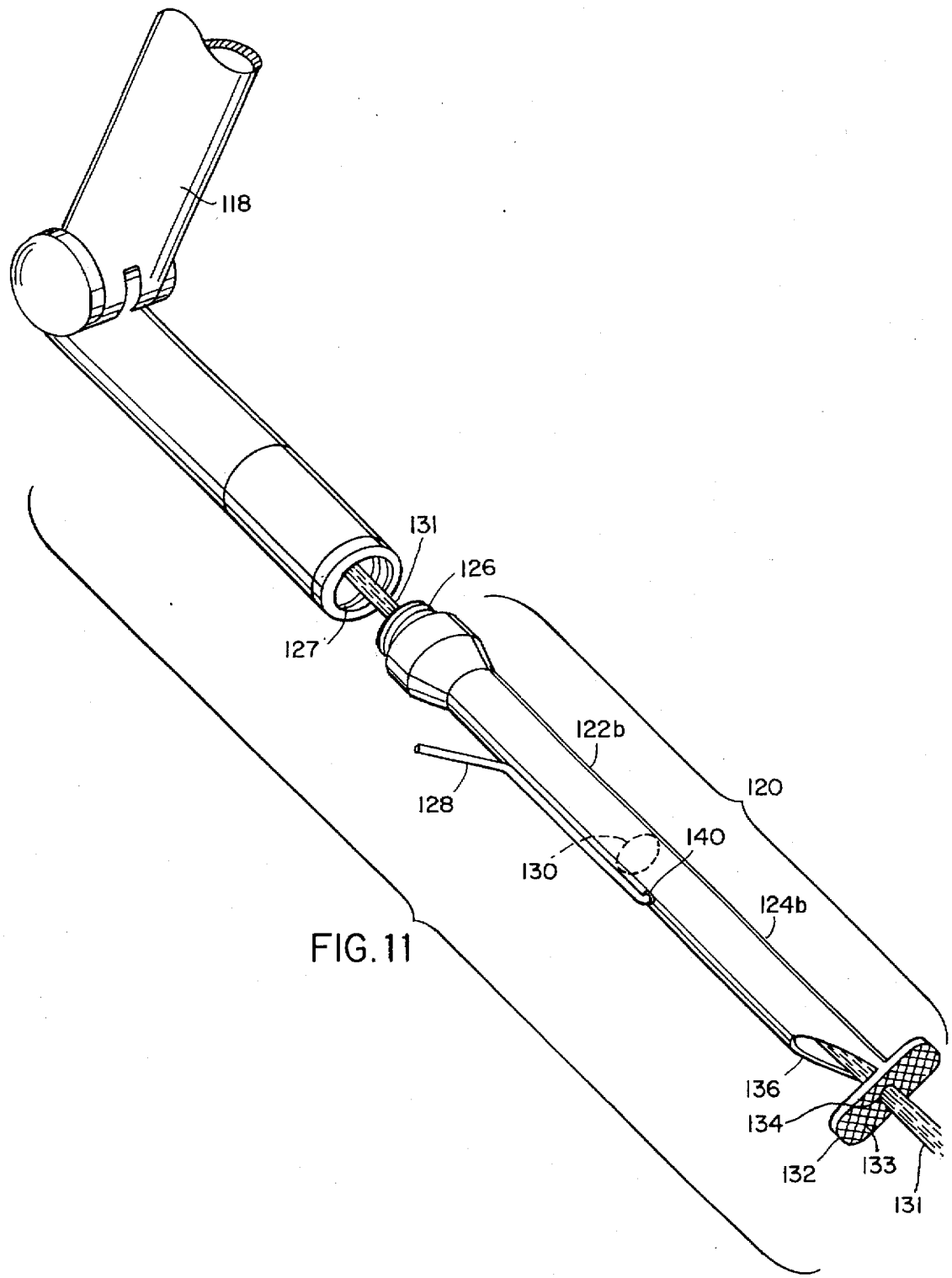
FIG. 11 is an enlarged, more detailed, exploded three-dimensional view of a portion of the articulated arm in FIG. 8 and another form of the handpiece in which the barrel and handpiece are integral.

While handpiece assembly 120, FIGS. 9 and 10, has been shown as including two separate sections, barrel 122 and handpiece 124 (124a), that is not a necessary limitation of the invention. Handpiece assembly 120b, FIG. 11, may be made as a single integral unit including both barrel 122b and handpiece 124b.

Although specific features of this invention are shown in some drawings and not others, this is for convenience only as each feature may be combined with any or all of the other features in accordance with the invention.

Other embodiments will occur to those skilled in the art and are within the following claims:

What is claimed is:

1. A thoracoscopic cannula system comprising:

a cannula having an enlarged limiter flange and an elongated hollow tube for insertion between the ribs of a thoracic patient; said tube including first and second opposed concave recess means for snap-fitting and interlocking with the adjacent ribs to securely anchor it; and an introducer including an elongated member slidably receivable in said hollow tube with a stop flange at one end to limit movement of said introducer through said tube and a beveled, blunted surface at the other end for gently penetrating and leading the cannula through an incision between the ribs of the patient.

2. The thoracoscopic cannula system of claim 1 in which said stop flange and limiter flange are coplanar to provide a common surface for applying an insertion force.

3. The thoracoscopic cannula system of claim 1 in which said introducer is generally oblong in cross-section.

4. The thoracoscopic cannula system of claim 1 in which said tube is beveled proximate said limiter flange for self-guiding said introducer and replacement instruments.

* * * * *